United States Patent
Li et al.

(10) Patent No.: US 12,167,962 B2
(45) Date of Patent: *Dec. 17, 2024

(54) VALVE LEAFLET ATTACHMENT IN COLLAPSIBLE PROSTHETIC VALVES

(71) Applicant: St. Jude Medical, Cardiology Division, Inc., St. Paul, MN (US)

(72) Inventors: Xue Mei Li, Shoreview, MN (US); Peter N. Braido, Wyoming, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/495,870

(22) Filed: Oct. 27, 2023

(65) Prior Publication Data
US 2024/0050226 A1 Feb. 15, 2024

Related U.S. Application Data

(63) Continuation of application No. 17/821,041, filed on Aug. 19, 2022, now Pat. No. 11,833,036, which is a
(Continued)

(51) Int. Cl.
*A61F 2/24* (2006.01)
(52) U.S. Cl.
CPC .............. *A61F 2/2415* (2013.01); *A61F 2/24* (2013.01); *A61F 2/2412* (2013.01); *A61F 2/2418* (2013.01); *A61F 2220/005* (2013.01); *A61F 2220/0066* (2013.01); *A61F 2220/0075* (2013.01); *A61F 2230/0054* (2013.01); *A61F 2230/008* (2013.01)

(58) Field of Classification Search
CPC ........ A61F 2/24; A61F 2/2412; A61F 2/2418; A61F 2/2415; A61F 2220/0075; A61F 2220/005; A61F 2220/0066; A61F 2230/008; A61F 2230/0054
See application file for complete search history.

(56) References Cited

U.S. PATENT DOCUMENTS 3,657,744 A 4/1972 Ersek
4,275,469 A 6/1981 Gabbay
(Continued)

FOREIGN PATENT DOCUMENTS

AU 2011202175 B1 7/2011
CN 101953725 A 1/2011
(Continued)

OTHER PUBLICATIONS

"Transluminal Implantation of Artificial Heart Valves", Andersen, H. R., et al., European Heart Journal, vol. 13, No. 5, May 1992, pp. 704-708.
(Continued)

*Primary Examiner* — Dinah Baria
(74) *Attorney, Agent, or Firm* — SLEMAN & LUND LLP

(57) ABSTRACT

A prosthetic heart valve includes a stent having a collapsed condition and an expanded condition. The stent includes a plurality of cells, each cell being formed by a plurality of struts, and a plurality of commissure features. The heart valve further includes a valve assembly secured to the stent and including a cuff and a plurality of leaflets, each leaflet being attached to adjacent commissure features and to the stent struts and/or the cuff.

18 Claims, 10 Drawing Sheets

Related U.S. Application Data continuation of application No. 16/929,173, filed on Jul. 15, 2020, now Pat. No. 11,452,596, which is a continuation of application No. 15/787,037, filed on Oct. 18, 2017, now Pat. No. 10,751,171, which is a continuation of application No. 14/568,697, filed on Dec. 12, 2014, now Pat. No. 9,827,091, which is a continuation of application No. 13/237,237, filed on Sep. 20, 2011, now Pat. No. 9,011,527.

(60) Provisional application No. 61/384,553, filed on Sep. 20, 2010.

(56) References Cited

U.S. PATENT DOCUMENTS

| | | |
|---|---|---|
| 4,491,986 A | 1/1985 | Gabbay |
| 4,580,568 A | 4/1986 | Gianturco |
| 4,759,758 A | 7/1988 | Gabbay |
| 4,878,906 A | 11/1989 | Lindemann |
| 4,922,905 A | 5/1990 | Strecker |
| 4,994,077 A | 2/1991 | Dobben |
| 5,078,720 A | 1/1992 | Burton |
| 5,391,172 A | 2/1995 | Williams |
| 5,411,552 A | 5/1995 | Andersen |
| 5,415,664 A | 5/1995 | Pinchuk |
| 5,456,667 A | 10/1995 | Ham |
| 5,480,423 A | 1/1996 | Ravenscroft |
| 5,480,424 A | 1/1996 | Cox |
| 5,484,444 A | 1/1996 | Braunschweiler |
| 5,702,418 A | 12/1997 | Ravenscroft |
| 5,824,041 A | 10/1998 | Lenker |
| 5,843,167 A | 12/1998 | Dwyer |
| 5,855,601 A | 1/1999 | Bessler |
| 5,935,163 A | 8/1999 | Gabbay |
| 5,961,549 A | 10/1999 | Nguyen |
| 5,980,533 A | 11/1999 | Holman |
| 6,077,297 A | 6/2000 | Robinson |
| 6,083,257 A | 7/2000 | Taylor |
| 6,090,140 A | 7/2000 | Gabbay |
| 6,214,036 B1 | 4/2001 | Letendre |
| 6,264,691 B1 | 7/2001 | Gabbay |
| 6,267,783 B1 | 7/2001 | Letendre |
| 6,269,819 B1 | 8/2001 | Oz |
| 6,368,348 B1 | 4/2002 | Gabbay |
| 6,391,050 B1 | 5/2002 | Broome |
| 6,419,695 B1 | 7/2002 | Gabbay |
| 6,458,153 B1 | 10/2002 | Bailey |
| 6,468,299 B2 | 10/2002 | Stack |
| 6,468,660 B2 | 10/2002 | Ogle |
| 6,488,702 B1 | 12/2002 | Besselink |
| 6,517,576 B2 | 2/2003 | Gabbay |
| 6,533,810 B2 | 3/2003 | Hankh |
| 6,582,464 B2 | 6/2003 | Gabbay |
| 6,610,088 B1 | 8/2003 | Gabbay |
| 6,623,518 B2 | 9/2003 | Thompson |
| 6,682,559 B2 | 1/2004 | Myers |
| 6,685,625 B2 | 2/2004 | Gabbay |
| 6,719,789 B2 | 4/2004 | Cox |
| 6,730,118 B2 | 5/2004 | Spenser |
| 6,736,845 B2 | 5/2004 | Marquez |
| 6,783,556 B1 | 8/2004 | Gabbay |
| 6,790,230 B2 | 9/2004 | Beyersdorf |
| 6,814,746 B2 | 11/2004 | Thompson |
| 6,830,584 B1 | 12/2004 | Seguin |
| 6,869,444 B2 | 3/2005 | Gabbay |
| 6,893,460 B2 | 5/2005 | Spenser |
| 6,908,481 B2 | 6/2005 | Cribier |
| 7,018,406 B2 | 3/2006 | Seguin |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo |
| 7,311,730 B2 | 12/2007 | Gabbay |
| 7,326,236 B2 | 2/2008 | Andreas |
| 7,329,278 B2 | 2/2008 | Seguin |
| 7,374,573 B2 | 5/2008 | Gabbay |
| 7,381,218 B2 | 6/2008 | Schreck |
| 7,399,315 B2 | 7/2008 | Iobbi |
| 7,419,501 B2 | 9/2008 | Brian |
| 7,452,371 B2 | 11/2008 | Pavcnik |
| 7,476,244 B2 | 1/2009 | Buzzard |
| 7,510,572 B2 | 3/2009 | Gabbay |
| 7,524,331 B2 | 4/2009 | Birdsall |
| RE40,816 E | 6/2009 | Taylor |
| 7,585,321 B2 | 9/2009 | Cribier |
| 7,682,390 B2 | 3/2010 | Seguin |
| 7,731,742 B2 | 6/2010 | Schlick |
| 7,803,185 B2 | 9/2010 | Gabbay |
| 7,846,203 B2 | 12/2010 | Cribier |
| 7,846,204 B2 | 12/2010 | Letac |
| 7,914,569 B2 | 3/2011 | Nguyen |
| 7,993,384 B2 | 8/2011 | Wu |
| 8,043,353 B2 | 10/2011 | Kaufmann |
| D648,854 S | 11/2011 | Braido |
| D652,926 S | 1/2012 | Braido |
| D652,927 S | 1/2012 | Braido |
| D653,341 S | 1/2012 | Braido |
| D653,342 S | 1/2012 | Braido |
| D653,343 S | 1/2012 | Ness |
| D654,169 S | 2/2012 | Braido |
| D654,170 S | 2/2012 | Braido |
| D660,432 S | 5/2012 | Braido |
| D660,433 S | 5/2012 | Braido |
| D660,967 S | 5/2012 | Braido |
| 8,313,525 B2 | 11/2012 | Tuval |
| 8,353,955 B2 | 1/2013 | Styrc |
| 8,562,663 B2 | 10/2013 | Mearns |
| 8,568,475 B2 | 10/2013 | Nguyen |
| 8,652,202 B2 | 2/2014 | Alon |
| 8,679,174 B2 | 3/2014 | Ottma |
| 8,778,019 B2 | 7/2014 | Knippel |
| 8,790,386 B2 | 7/2014 | Dwork |
| 9,039,759 B2 | 5/2015 | Alkhatib |
| 2002/0036220 A1 | 3/2002 | Gabbay |
| 2002/0045936 A1 | 4/2002 | Moe |
| 2002/0183827 A1 | 12/2002 | Derus |
| 2003/0023303 A1 | 1/2003 | Palmaz |
| 2003/0040792 A1 | 2/2003 | Gabbay |
| 2003/0050694 A1 | 3/2003 | Yang |
| 2003/0130726 A1 | 7/2003 | Thorpe |
| 2003/0144725 A1 | 7/2003 | Lombardi |
| 2004/0039436 A1 | 2/2004 | Spenser |
| 2004/0049262 A1 | 3/2004 | Obermiller |
| 2004/0093060 A1 | 5/2004 | Seguin |
| 2004/0093075 A1 | 5/2004 | Kuehne |
| 2004/0148009 A1 | 7/2004 | Buzzard |
| 2004/0186563 A1 | 9/2004 | Lobbi |
| 2004/0210304 A1 | 10/2004 | Seguin |
| 2004/0260390 A1 | 12/2004 | Sarac |
| 2005/0004583 A1 | 1/2005 | Oz |
| 2005/0049667 A1 | 3/2005 | Arbefeuille |
| 2005/0080476 A1 | 4/2005 | Gunderson |
| 2005/0096726 A1 | 5/2005 | Sequin |
| 2005/0137687 A1 | 6/2005 | Salahieh |
| 2005/0137688 A1 | 6/2005 | Salahieh |
| 2005/0137691 A1 | 6/2005 | Salahieh |
| 2005/0137695 A1 | 6/2005 | Salahieh |
| 2005/0137697 A1 | 6/2005 | Salahieh |
| 2005/0240200 A1 | 10/2005 | Bergheim |
| 2005/0240254 A1 | 10/2005 | Austin |
| 2005/0256566 A1 | 11/2005 | Gabbay |
| 2006/0008497 A1 | 1/2006 | Gabbay |
| 2006/0025857 A1 | 2/2006 | Bergheim |
| 2006/0025913 A1 | 2/2006 | Horikawa |
| 2006/0058872 A1 | 3/2006 | Salahieh |
| 2006/0074484 A1 | 4/2006 | Huber |
| 2006/0122692 A1 | 6/2006 | Gilad |
| 2006/0149360 A1 | 7/2006 | Schwammenthal |
| 2006/0173532 A1 | 8/2006 | Flagle |
| 2006/0178740 A1 | 8/2006 | Stacchino |
| 2006/0195180 A1 | 8/2006 | Kheradvar |
| 2006/0206202 A1 | 9/2006 | Bonhoeffer |

(56) References Cited

U.S. PATENT DOCUMENTS

| | | |
|---|---|---|
| 2006/0241744 A1 | 10/2006 | Beith |
| 2006/0241745 A1 | 10/2006 | Solem |
| 2006/0259120 A1 | 11/2006 | Vongphakdy |
| 2006/0259136 A1 | 11/2006 | Nguyen |
| 2006/0259137 A1 | 11/2006 | Artof |
| 2006/0265056 A1 | 11/2006 | Nguyen |
| 2006/0276813 A1 | 12/2006 | Greenberg |
| 2006/0282150 A1 | 12/2006 | Olson |
| 2006/0282157 A1 | 12/2006 | Hill |
| 2007/0010876 A1 | 1/2007 | Salahieh |
| 2007/0027534 A1 | 2/2007 | Bergheim |
| 2007/0043435 A1 | 2/2007 | Seguin |
| 2007/0055358 A1 | 3/2007 | Krolik |
| 2007/0067029 A1 | 3/2007 | Gabbay |
| 2007/0093890 A1 | 4/2007 | Eliasen |
| 2007/0100435 A1 | 5/2007 | Case |
| 2007/0118210 A1 | 5/2007 | Pinchuk |
| 2007/0156225 A1 | 7/2007 | George |
| 2007/0213813 A1 | 9/2007 | Von Segesser |
| 2007/0233228 A1 | 10/2007 | Eberhardt |
| 2007/0244545 A1 | 10/2007 | Birdsall |
| 2007/0244552 A1 | 10/2007 | Salahieh |
| 2007/0260301 A1 | 11/2007 | Chuter |
| 2007/0288087 A1 | 12/2007 | Fearnot |
| 2008/0004688 A1 | 1/2008 | Spenser |
| 2008/0004696 A1 | 1/2008 | Vesely |
| 2008/0009940 A1 | 1/2008 | Cribier |
| 2008/0021552 A1 | 1/2008 | Gabbay |
| 2008/0039934 A1 | 2/2008 | Styrc |
| 2008/0071369 A1 | 3/2008 | Tuval |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey |
| 2008/0140189 A1 | 6/2008 | Nguyen |
| 2008/0147179 A1 | 6/2008 | Cai |
| 2008/0147183 A1 | 6/2008 | Styrc |
| 2008/0154355 A1 | 6/2008 | Benichou |
| 2008/0154356 A1 | 6/2008 | Obermiller |
| 2008/0177381 A1 | 7/2008 | Navia |
| 2008/0228264 A1 | 9/2008 | Li |
| 2008/0243245 A1 | 10/2008 | Thambar |
| 2008/0255662 A1 | 10/2008 | Stacchino |
| 2008/0262602 A1 | 10/2008 | Wilk |
| 2008/0269878 A1 | 10/2008 | Iobbi |
| 2008/0269879 A1 | 10/2008 | Sathe |
| 2008/0275540 A1 | 11/2008 | Wen |
| 2009/0112309 A1 | 4/2009 | Jaramillo |
| 2009/0118826 A1 | 5/2009 | Khaghani |
| 2009/0138079 A1 | 5/2009 | Tuval |
| 2009/0157175 A1 | 6/2009 | Benichou |
| 2009/0216312 A1 | 8/2009 | Straubinger |
| 2009/0240320 A1 | 9/2009 | Tuval |
| 2009/0287299 A1 | 11/2009 | Tabor |
| 2010/0004740 A1 | 1/2010 | Seguin |
| 2010/0036484 A1 | 2/2010 | Hariton |
| 2010/0049306 A1 | 2/2010 | House |
| 2010/0049313 A1 | 2/2010 | Alon |
| 2010/0082094 A1 | 4/2010 | Quadri |
| 2010/0087907 A1 | 4/2010 | Lattouf |
| 2010/0114305 A1 | 5/2010 | Kang |
| 2010/0121434 A1 | 5/2010 | Paul |
| 2010/0131055 A1 | 5/2010 | Case |
| 2010/0168778 A1 | 7/2010 | Braido |
| 2010/0168839 A1 | 7/2010 | Braido |
| 2010/0185277 A1 | 7/2010 | Braido |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau |
| 2010/0249911 A1 | 9/2010 | Alkhatib |
| 2010/0249923 A1 | 9/2010 | Alkhatib |
| 2010/0262231 A1 | 10/2010 | Tuval |
| 2010/0286768 A1 | 11/2010 | Alkhatib |
| 2010/0298931 A1 | 11/2010 | Quadri |
| 2011/0029072 A1 | 2/2011 | Gabbay |
| 2011/0208298 A1 | 8/2011 | Tuval |
| 2011/0282425 A1 | 11/2011 | Dwork |
| 2011/0288626 A1 | 11/2011 | Straubinger |
| 2011/0295216 A1 | 12/2011 | Miller |
| 2012/0022635 A1 | 1/2012 | Yamashita |
| 2012/0053574 A1 | 3/2012 | Murray, III |
| 2012/0071969 A1 | 3/2012 | Li |
| 2012/0078352 A1 | 3/2012 | Wang |
| 2012/0089223 A1 | 4/2012 | Nguyen |
| 2012/0197391 A1 | 8/2012 | Alkhatib |
| 2012/0310332 A1 | 12/2012 | Murray |
| 2013/0030520 A1 | 1/2013 | Lee |
| 2013/0079869 A1 | 3/2013 | Straubinger |
| 2014/0067050 A1 | 3/2014 | Costello |
| 2014/0135909 A1 | 5/2014 | Carr |

FOREIGN PATENT DOCUMENTS

| | | |
|---|---|---|
| DE | 20000659 U1 | 5/2001 |
| DE | 19857887 B4 | 5/2005 |
| DE | 10121210 B4 | 11/2005 |
| DE | 102005003632 A1 | 8/2006 |
| DE | 202008009610 U1 | 12/2008 |
| EP | 0051451 A2 | 5/1982 |
| EP | 0850607 A1 | 7/1998 |
| EP | 0856300 A1 | 8/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1360942 B1 | 12/2005 |
| EP | 1872743 A1 | 1/2008 |
| EP | 1926455 A2 | 6/2008 |
| EP | 1229865 B1 | 11/2010 |
| FR | 2850008 A1 | 7/2004 |
| FR | 2847800 B1 | 10/2005 |
| JP | 2008539985 A | 11/2008 |
| JP | 2010528761 A | 8/2010 |
| JP | 2010540079 A | 12/2010 |
| WO | 9117720 A1 | 11/1991 |
| WO | 9716133 A1 | 5/1997 |
| WO | 9832412 A2 | 7/1998 |
| WO | 1998029057 A1 | 7/1998 |
| WO | 9913801 A1 | 3/1999 |
| WO | 9930646 A1 | 6/1999 |
| WO | 0044313 A1 | 8/2000 |
| WO | 0069368 A2 | 11/2000 |
| WO | 0119285 A1 | 3/2001 |
| WO | 2001028459 A1 | 4/2001 |
| WO | 0149213 A2 | 7/2001 |
| WO | 0156500 A2 | 8/2001 |
| WO | 2001054625 A1 | 8/2001 |
| WO | 2001076510 A2 | 10/2001 |
| WO | 2002036048 A1 | 5/2002 |
| WO | 0247575 A2 | 6/2002 |
| WO | 02067782 A2 | 9/2002 |
| WO | 2003047468 A1 | 6/2003 |
| WO | 2005070343 A1 | 8/2005 |
| WO | 2006073626 A2 | 7/2006 |
| WO | 2007071436 A2 | 6/2007 |
| WO | 2008042266 A2 | 4/2008 |
| WO | 2008070797 A2 | 6/2008 |
| WO | 2008125153 A1 | 10/2008 |
| WO | 2008138584 A1 | 11/2008 |
| WO | 2008150529 A1 | 12/2008 |
| WO | 2009029199 A1 | 3/2009 |
| WO | 2009042196 A2 | 4/2009 |
| WO | 2009045338 A1 | 4/2009 |
| WO | 2009061389 A2 | 5/2009 |
| WO | 2009091509 A1 | 7/2009 |
| WO | 2009149462 A2 | 12/2009 |
| WO | 2010008548 A2 | 1/2010 |
| WO | 2010008549 A1 | 1/2010 |
| WO | 2010037141 A1 | 4/2010 |
| WO | 2010096176 A1 | 8/2010 |
| WO | 2010098857 A1 | 9/2010 |

(56) References Cited

FOREIGN PATENT DOCUMENTS

| WO | 2012026965 A2 | 3/2012 |
|---|---|---|
| WO | 2012036741 A2 | 3/2012 |

OTHER PUBLICATIONS

Alkhatib, U.S. Appl. No. 13/216,124, filed Aug. 23, 2011, titled "Leaflet Suturing To Commissure Points For Prosthetic Heart Valve".
Andersen HR, Knudsen LL, Hasenkam JM. Transluminal implantation of artificial heart valves. Description of a new expandable aortic valve and initial results with implantation by catheter technique in closed chest pigs. European heart Journal. May 1, 1992;13(5):704-8.
Andersen, Henning Rud, Transluminal Catheter Implanted Prosthetic Heart Valves, International Journal of Angiology 7:102-106 (1998).
Australian Examination Report for Application No. 2011293898 dated Jul. 26, 2013, 3 pages.
Braido, et al., U.S. Appl. No. 29/375,243, filed Sep. 20, 2010, titled "Surgical Stent Assembly".
Dewey, et al., "Transapical Aortic Valve Implantation: An Animal Feasibility Study", The Annals of Thoracic Surgery, vol. 82, No. 1, Jul. 2006, pp. 110-116.
European Search Report for Application No. EP 21165142, dated Jul. 8, 2021, 7 pages.
Gundiah, Namrata et al., "Asymmetric mechanical properties of porcine aortic sinuses," The Annals of Thoracic Surgery, 85.5 (2008), 1631-1638.
Gundiah, Namrata et la., "Significant material property differences between the porcine ascending aorta and aortic sinuses," Journal of Heart Valve Disease, 17.6 (2008), 606-613.
Hijazi et al., Transcatheter Valve Repair, CRC Press, Jan. 2006, pp. 165-186.
Huber, et al., "Direct-Access Valve Replacement: A Novel Approach for Off-Pump Valve Implantation Using Valved Stents", Journal of the American College of Cardiology, vol. 46, No. 2, Jul. 2005, pp. 366-370.
International Search Report and Written Opinion for Application No. PCT/US2011/048963, dated Dec. 15, 2011.
International Search Report and Written Opinion for Application No. PCT/US2011/001450 dated Mar. 5, 2012. 7 pages.
International Search Report and Written Opinion for Application No. PCT/US2011/001615 dated Jul. 11, 2012. 12 pages.
International Search Report and Written Opinion for Application No. PCT/US2011/048967, dated Dec. 15, 2011. 13 pages.
International Search Report and Written Opinion for Application No. PCT/US2011/048989, dated Dec. 15, 2011. 15 pages.
International Search Report and Written Opinion for Application No. PCT/US2013/039407 dated Feb. 10, 2014. 15 pages.
International Search Report for Application No. PCT/US2011/001597 dated Mar. 7, 2012. 7 pages.
Knippel, U.S. Appl. No. 13/234,782, filed on Sep. 16, 2011, titled "Staged Deployment Devices And Method For Transcatheter Heart Valve Delivery".
Knudsen LL, Andersen HR, Hasenkam JM. Catheter-Implanted Prosthetic Heart Valves: Transluminal catheter Implantation of a new expandable artificial heart valve in the descending thoracic aorta in isolated vessels and closed chest pigs. The International Journal of Artificial Organs. May 1993; 16(5):253-62.
Mack, "Minimally invasive cardiac surgery", Surgical Endoscopy, 2006, 20:S488-S492, DOI: 10.1007/s00464-006-0110-8, presented Apr. 24, 2006.
Martin, Caitlin, Thuy Pham, and Wei Sun, "Significant differences in the material properties between aged human and porcine aortic tissues," European Journal of Cardio-Thoracic Surgery, 40.1 (2011), 28-34.
Moazami et al., "Transluminal Aortic Valve Placement: A Feasibility Study With a Newly designed Collapsible Aortic Valve.", ASAIO Journal, (Sep. 1996), vol. 42, pp. M381-M385.
Morris, U.S. Appl. No. 13/788,820, filed Mar. 7, 2013, titled "Devices And Methods For Transcatheter Heart Valve Delivery".
Overview of PRE-CE Mark Transcatheter Aortic Valve Technologies (powerpoint-dated Jun. 1, 2010). 14 pages.
Pavcnik et al., "Aortic and venous valve for percutaneous insertion", Minimally Invasive Therapy & Allied Technologies, 9:3-4 (2000), 287-292.
Quaden et al., "Percutaneous aortic valve replacement: resection before implantation", European J. of Cardio-thoracic Surgery, vol. 27, Issue 5, pp. 836-840, May 2005.
Samuel V. Lichtenstein et al., Transapical Transcatheter Aortic Valve Implantation in Humans, Circulation, Jul. 2006, pp. 591-596, vol. 114.
Samuel V. Lichtenstein, "Closed heart surgery: Back to the future", The Journal of Thoracic and Cardiovascular Surgery, vol. 131, No. 5, pp. 941-943, May 2006.
Sauren, A.A.H.J. et al., "The mechanical properties of porcine aortic valve tissues," Journal of Biomechanics, 16.5 1983), 327-337.
U.S. Appl. No. 29/375,232, filed Sep. 20, 2010.
U.S. Appl. No. 29/375,253, filed Sep. 20, 2010.
U.S. Appl. No. 29/375,257, filed Sep. 20, 2010.
U.S. Appl. No. 29/375,260, filed Sep. 20, 2010.
Walther et al., "Transapical approach for sutureless stent-fixed aortic valve implantation: experimental results", European Journal of Cardio-thoracic Surgery, vol. 29(5), pp. 703-708 (Jan. 30, 2006).
Wang, U.S. Appl. No. 13/212,442, filed Aug. 18, 2011, titled "Staged Deployment Devices And Methods For Transcatheter Heart Valve Delivery Systems".
Webb et al., "Percutaneous Aortic Valve Implantation Retrograde From the Femoral Artery", Circulation, published online Feb. 2006, pp. 842-850, vol. 113, American Heart Association, Dallas, TX, USA.
Zegdi, Rachid, MD, PhD et al., "Is It Reasonable to Treat All Calcified Stenotic Aortic Valves With a Valved Stent?" 579-584, J. of the American College of Cardiology, vol. 51. No. 5, Feb. 5, 2008.

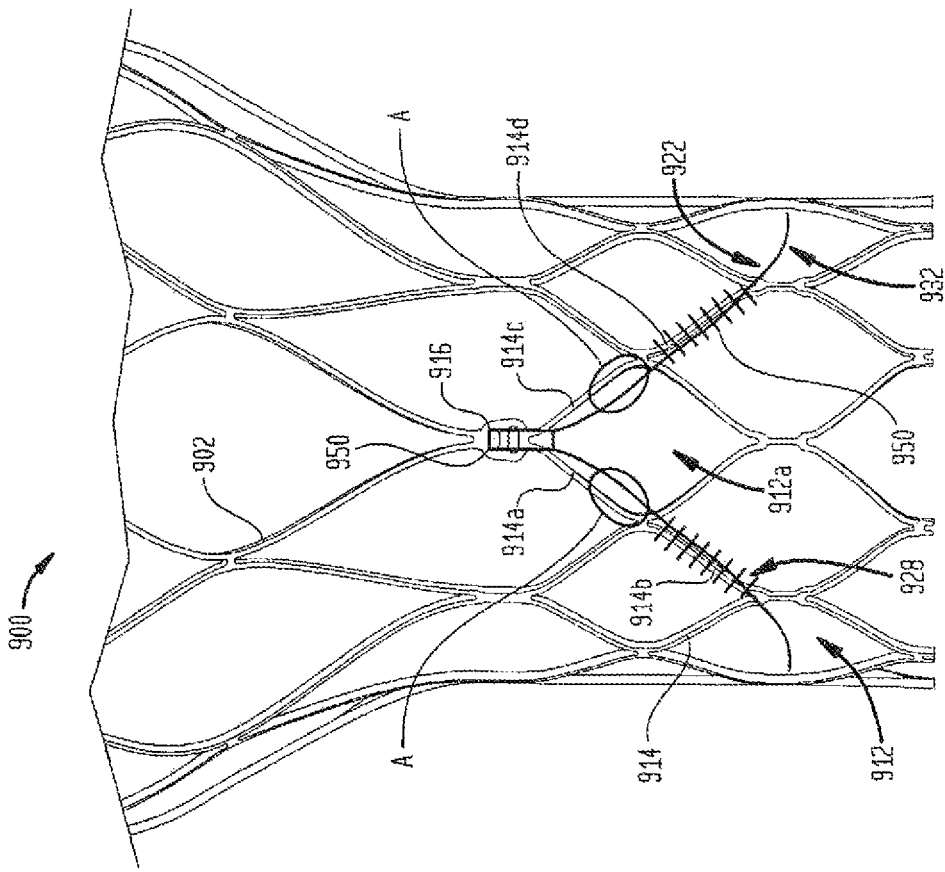
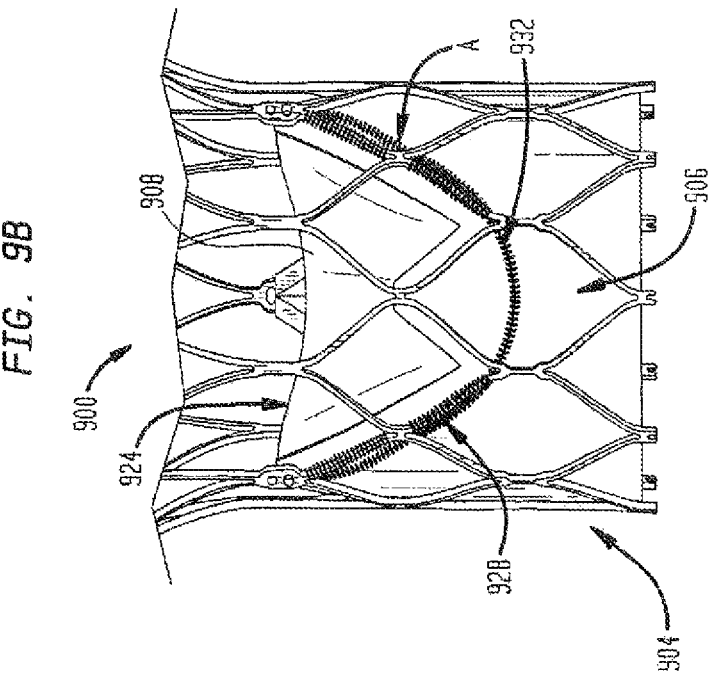
FIG. 9A
FIG. 9B

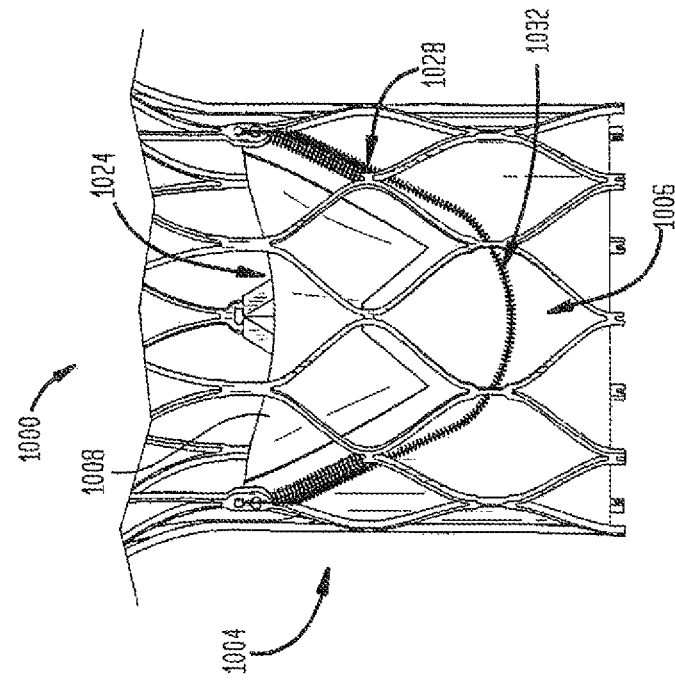
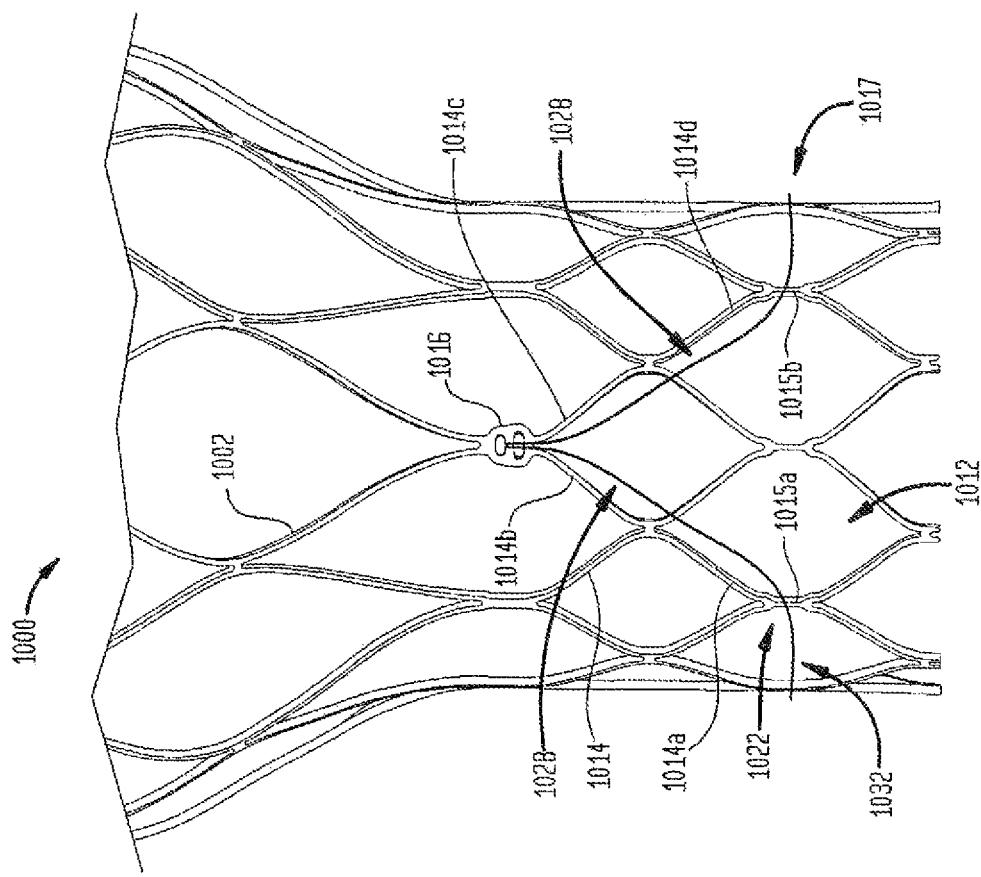

VALVE LEAFLET ATTACHMENT IN COLLAPSIBLE PROSTHETIC VALVES

CROSS-REFERENCE TO RELATED APPLICATIONS

This application is a continuation of U.S. patent application Ser. No. 17/821,041, filed Aug. 19, 2022, which is a continuation of U.S. patent application Ser. No. 16/929,173, filed Jul. 15, 2020, now U.S. Pat. No. 11,452,596, issued Sep. 27, 2022, which is a continuation of U.S. Pat. No. 10,751,171, filed Oct. 18, 2017, which is a continuation of U.S. Pat. No. 9,827,091, filed Dec. 12, 2014, which is a continuation of U.S. Pat. No. 9,011,527, filed Sep. 20, 2011, which claims the benefit of the filing date of U.S. Provisional Patent Application No. 61/384,553 filed Sep. 20, 2010, the disclosures of which are hereby incorporated herein by reference.

BACKGROUND OF THE INVENTION

The present invention relates to heart valve replacement and, in particular, to collapsible prosthetic heart valves. More particularly, the present invention relates to collapsible prosthetic heart valves having unique valve leaflet attachments.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

Despite the various improvements that have been made to collapsible prosthetic heart valves, the currently available devices suffer from some shortcomings. For example, anatomical variations between patients may prevent adequate coaptation of the heart valve leaflets, and may further result in increased stresses at different portions of the heart valve, leading to valve failure. In addition, conventional delivery devices do not allow for sufficient operability of the valve leaflets during partial deployment.

There therefore is a need for further improvements in collapsible prosthetic heart valves and their method of manufacture. Among other advantages, the present invention may address one or more of these needs.

BRIEF SUMMARY OF THE INVENTION

The present disclosure is related to prosthetic heart valves. In one embodiment, the prosthetic heart valve includes a stent and a valve assembly. The stent has a collapsed condition and an expanded condition, the stent having a proximal end, a distal end and a plurality of cells. Each cell is formed by a plurality of struts. The valve assembly is secured to the stent and includes a cuff and a plurality of leaflets. Each leaflet has a folded portion and is coupled to the cuff at the folded portion.

In one example, the folded portion has a width between a folded edge and a free edge, the width being between about 0.1 mm and about 2 mm. In another example, the folded portion of each of the plurality of leaflets is sutured to the cuff using a whip stitch. In another example, the stent includes a plurality of commissure features and each leaflet is sutured to the cuff through the folded portion with a repeating suture pattern. The pattern includes a descending seam, an ascending seam, and a vertex between the descending seam and the ascending seam. The pattern is disposed solely between the commissure features and the proximal end of the stent.

In another embodiment, the prosthetic heart valve includes a valve assembly and a stent having a collapsed condition and an expanded condition. The stent includes a plurality of cells. Each cell is formed by a plurality of struts. The valve assembly is secured to the stent and includes a cuff and a plurality of leaflets. Each leaflet includes a first edge adjacent to the cuff and a second edge spaced apart from the cuff. Each leaflet is attached to the stent such that at least a portion of the first edge of each leaflet is disposed along at least one strut of the stent.

BRIEF DESCRIPTION OF THE DRAWINGS

Various embodiments of the present devices are disclosed herein with reference to the drawings, wherein:

FIG. 9A is a developed view of a portion of a collapsible prosthetic heart valve according to still another embodiment of the present invention having some portions of the leaflets of the valve assembly attached to the stent and disposed substantially along certain stent struts;

FIG. 9B is a partial side view of the collapsible prosthetic heart valve of FIG. 9A;

FIG. 10A is a developed view of a portion of a collapsible prosthetic heart valve according to yet a further embodiment of the present invention in which portions of the leaflets of the valve assembly are attached to the cuff at a substantially uniform distance from the stent struts; and FIG. 10B is a partial side view of the collapsible prosthetic heart valve of FIG. 10A.

Various embodiments of the present invention will now be described with reference to the appended drawings. It is to be appreciated that these drawings depict only some embodiments of the invention and are therefore not to be considered limiting of its scope.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve into a patient, the terms "proximal" and "distal" are to be taken as relative to the user of the delivery devices. "Proximal" is to be understood as relatively close to the user, and "distal" is to be understood as relatively farther away from the user.

Figure 1A:
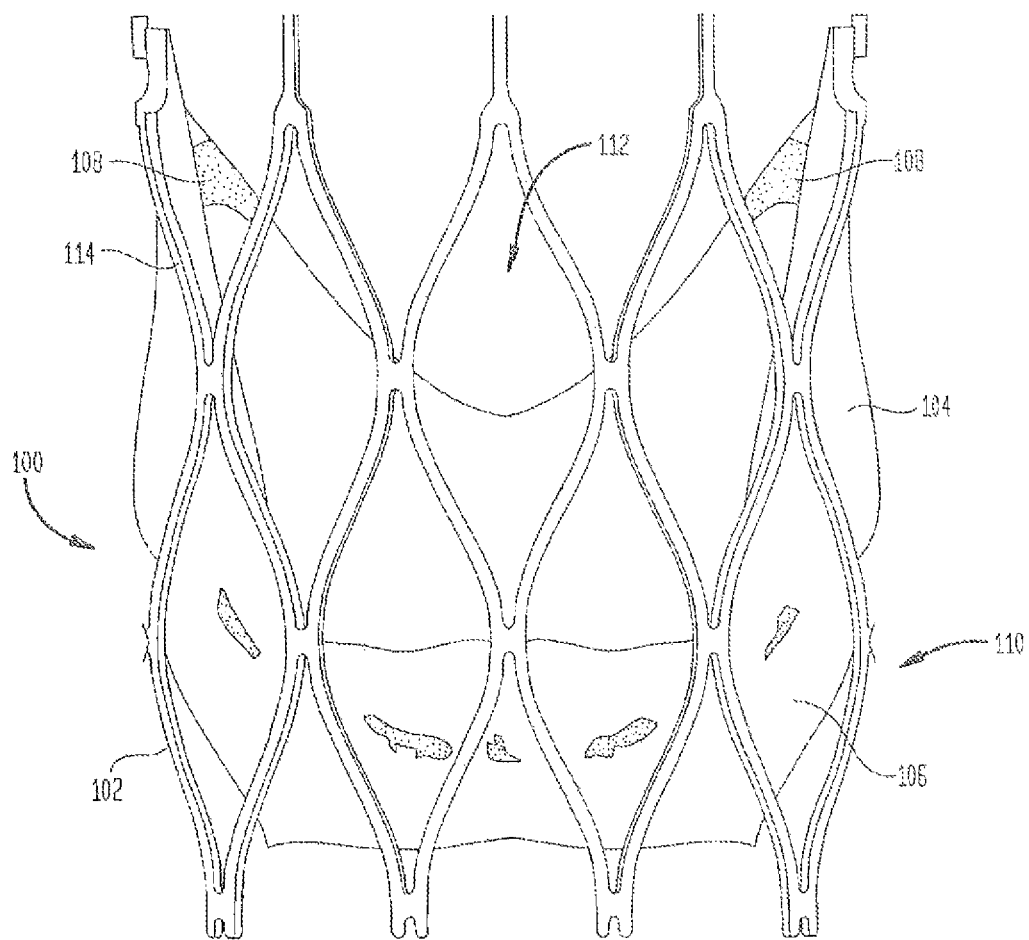
FIG. 1A is a partial side view of a conventional prosthetic heart valve showing the strain distribution in the valve assembly.

FIG. 1A shows a typical collapsible prosthetic heart valve 100. The prosthetic heart valve 100 is designed to replace the function of a native aortic valve of a patient. Examples of collapsible prosthetic heart valves are described in International Patent Application Publication No. WO/2009/042196; U.S. Pat. Nos. 7,018,406; and 7,329,278, the disclosures of all of which are hereby incorporated herein by reference. As discussed in detail below, the prosthetic heart valve has an expanded condition and a collapsed condition. Although the invention is described herein as applied to a prosthetic heart valve for replacing a native aortic valve, the invention is not so limited, and may be applied to prosthetic valves for replacing other types of cardiac valves.

The prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. The stent 102 may have an annulus section 110, an aortic section (not shown), and an intermediate section disposed between the annulus and aortic sections. Each of the annulus section 110, the intermediate section, and the aortic section of the stent 102 includes a plurality of cells 112 connected to one another around the stent. The annulus section 110, the intermediate section, and the aortic section of the stent 102 may include one or more annular rows of cells 112 connected to one another. For instance, the annulus section 110 may have two annular rows of cells 112. When the prosthetic heart valve 100 is in the expanded condition, each cell 112 may be substantially diamond shaped. Regardless of its shape, each cell 112 is formed by a plurality of struts 114. For example, a cell 112 may be formed by four struts 114.

The stent 102 may include commissure features or commissure posts (not shown) connecting at least two cells 112 in the longitudinal direction of the stent 102. The commissure features may include eyelets that facilitate the suturing of a valve assembly 104 to the stent 102.

The prosthetic heart valve 100 also includes a valve assembly 104 attached inside the annulus section 110 of the stent 102. United States Patent Application Publication No. 2008/0228264, filed Mar. 12, 2007, and United States Patent Application Publication No. 2008/0147179, filed Dec. 19, 2007, the entire disclosures of both of which are hereby incorporated herein by reference, describe suitable valve assemblies. The valve assembly 104 may be wholly or partly formed of any suitable biological material or polymer. Examples of biological materials suitable for the valve assembly 104 include, but are not limited to, porcine or bovine pericardial tissue. Examples of polymers suitable for the valve assembly 104 include, but are not limited to, polyurethane and polyester.

The valve assembly 104 may include a cuff 106 disposed on the lumenal surface of annulus section 110, on the ablumenal surface of the annulus section, or on both surfaces, and the cuff may cover all or part of either or both of the lumenal and ablumenal surfaces of the annulus section. FIG. 1A shows cuff 106 disposed on the lumenal surface of annulus section 110 so as to cover part of the annulus section while leaving another part thereof uncovered. In addition to the materials for forming valve assembly 104 noted above, the cuff 106 and/or any of the sutures described herein may include ultra-high-molecular-weight polyethylene. The valve assembly 104 may further include a plurality of leaflets 108 which collectively function as a one-way valve.

Figure 1B:
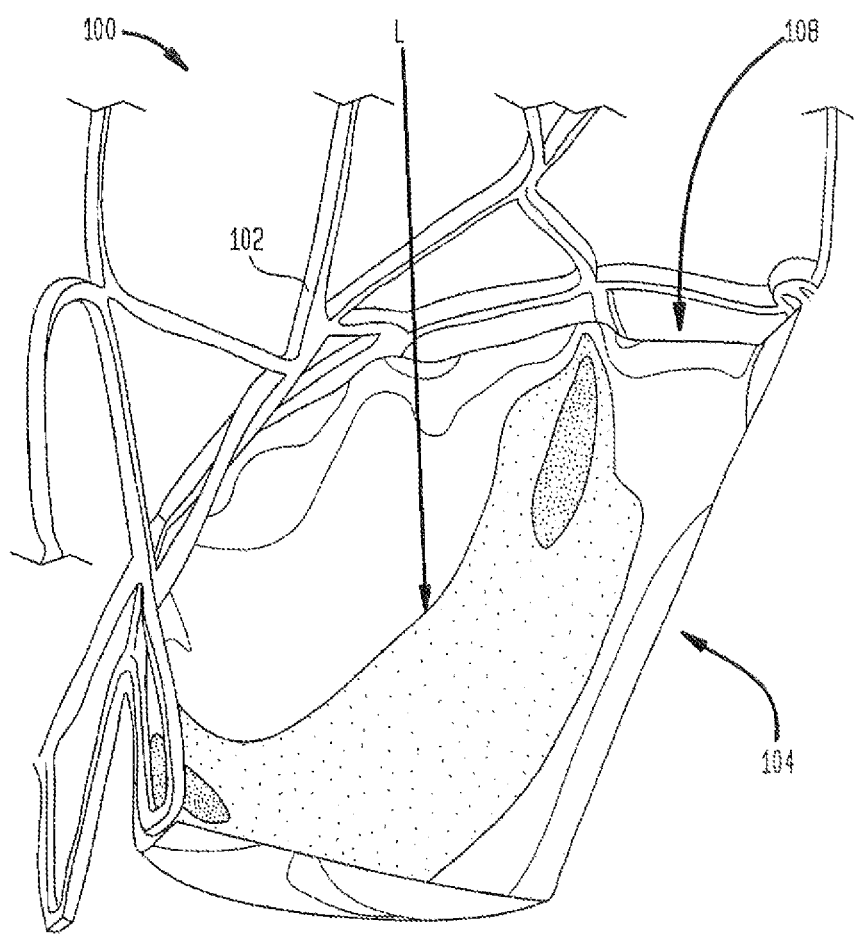
FIG. 1B is an enlarged partial view of the conventional prosthetic heart valve of FIG. 1A showing the strain distribution in the cuff.

The cuff 106 of the prosthetic heart valve 100 of FIG. 1A tends to experience relatively high strain and/or stress at certain locations. In such heart valves 100, the weight of the leaflets 108 may subject the cuff 106 to a load in the direction indicated by arrow L, shown in FIG. 1B. This load may cause an abnormally high stress and/or strain on the cuff. To manage the increased stress and strain on the cuff 106, some conventional heart valves 100 have made the cuff 106 thicker. However, thicker cuffs generally lead to a larger heart valve that is more difficult to deliver and implant. Moreover, a bulky prosthetic heart valve is typically incapable of being tested in vivo.

Another method of redistributing the load has been to attach the leaflets to the struts. This too has been problematic. For a host of reasons outlined below, in accordance with some embodiments of the present invention, it may be advantageous to attach the leaflets substantially entirely to the cuff and not to the struts.

First, in certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid disease, and/or valve insufficiency may not be able to be treated well, if at all, with the current collapsible designs.

Implantation of a prosthetic valve adjacent unevenly calcified leaflets could lead to several problems such as: (1) perivalvular leakage (PV leak), (2) valve migration, (3) mitral valve impingement, (4) conduction system disruption, (5) coronary blockage, etc., all of which can have severely adverse clinical outcomes. To reduce these adverse events, the optimal valve would seal and anchor adequately without the need for excessive radial force, protrusion into the left ventricular outflow tract (LVOT), etc., that could harm nearby anatomy and physiology. Embodiments of the present invention which attach the leaflets mainly to the cuff are able to achieve better coaptation of the leaflets, reducing the risk of leakage.

Second, the annulus section of the prosthetic valve may have a generally regular cylindrical shape by which is meant that the structure has a generally circular cross-section with a substantially constant diameter along its length. When placed in the annulus of a native heart valve, such as, for example, the tricuspid aortic valve, and expanded, a substantially fluid-tight fit should result. However, the native valve annulus may not be circular, and, in fact, may vary from patient to patient, as may the shape of the aortic sinus or aorta, the angle of the junction between the valve annulus and the aortic sinus, and other local anatomical features. When a prosthetic valve is deployed and expanded, it must accommodate these anatomical variations in order to function properly. This may result in distortion of the shape of the stent and/or valve assembly, and the repositioning of leaflets relative to one another, which can affect the coaptation of these leaflets.

As the stent of a collapsible prosthetic heart valve distorts during implantation, during beating of the heart, or because of irregularities in the patient's anatomy or the condition of the native valve, such distortion may be translated to the valve assembly, such that not all of the valve leaflets meet to form effective coaptation junctions. This can result in leakage or regurgitation and other inefficiencies which can reduce cardiac performance. Moreover, if the prosthetic valve is not placed optimally and the valve leaflets are not coapting as intended, other long term effects, such as uneven wear of the individual leaflets, can be postulated.

Prosthetic valves in accordance with certain aspects of the present invention, however, can function properly notwithstanding the distortion of the stent and/or valve assembly because the leaflets are substantially attached to the cuff and not to the stent. Without wishing to be held to any particular theory, it is believed that a valve design having leaflets mostly sewn to the cuff may be better able to adjust to less than perfect annulus geometry. Such leaflet-cuff arrangements may be more insulated from imperfect geometry-induced stresses on the struts than those arrangements having the leaflets completely or predominantly sewn to the stent. Thus, the possibility of uneven wear due to anatomical variations is greatly reduced by attaching the leaflets entirely or predominantly to the cuff.

Moreover, by sewing the leaflet to the cuff and not to the struts, greater flexibility is afforded in positioning the leaflets and in varying the height, width and shape of the leaflets. Specifically, because the leaflets in conventional heart valves are attached to the struts, the leaflet shape and positioning is limited by the location of the struts. In contrast, suturing patterns may be varied with greater benefits when the leaflets are attached predominantly to the cuff.

Having outlined some of the benefits of a leaflet-cuff attachment, the features of this embodiment will be described in connection with the prosthetic heart valve 300 shown in FIGS. 2A-5. It will also be noted that while the inventions herein described are predominately discussed in terms of a tricuspid valve and a stent having a shape as illustrated in FIGS. 2A-5, the valve could be a bicuspid valve, such as the mitral valve, and the stent could have different shapes, such as a flared or conical annulus section, a less-bulbous aortic section, and the like, and a differently shaped intermediate section.

In attaching the plurality of leaflets, each leaflet 308 may be first attached to the stent 302 by suturing through the eyelets of commissure features 316. Additional examples of leaflet-commissure feature attachments are disclosed in U.S. patent application Ser. No. 13/216,124, entitled "Leaflet Suturing to Commissure features for Prosthetic Heart Valve", filed on Aug. 23, 2011, the disclosure of which is hereby incorporated by reference as if fully set forth herein. In addition to the commissure features 316, the plurality of leaflets may be attached to the cuff 306 as described below.

Figure 2A:
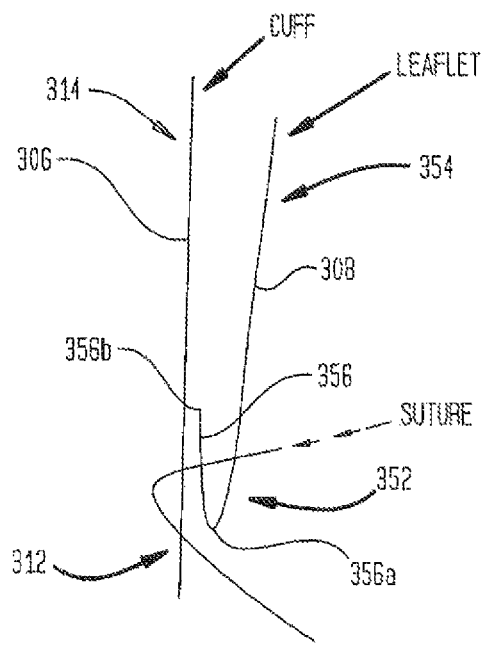
FIG. 2A is a highly schematic view of a portion of a collapsible prosthetic heart valve according to one embodiment of the present invention having folded leaflets sutured to the cuff.
Figure 2B:
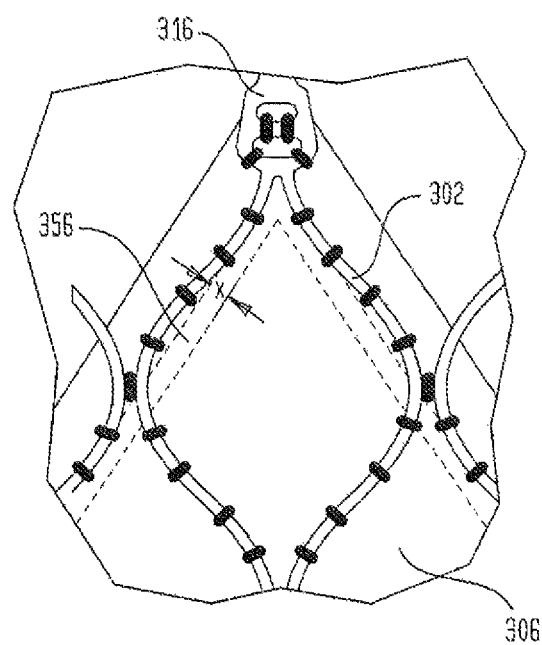
FIG. 2B is an enlarged side view of a portion of the collapsible prosthetic heart valve of FIG. 2A showing a folded belly flap.
Figure 3:
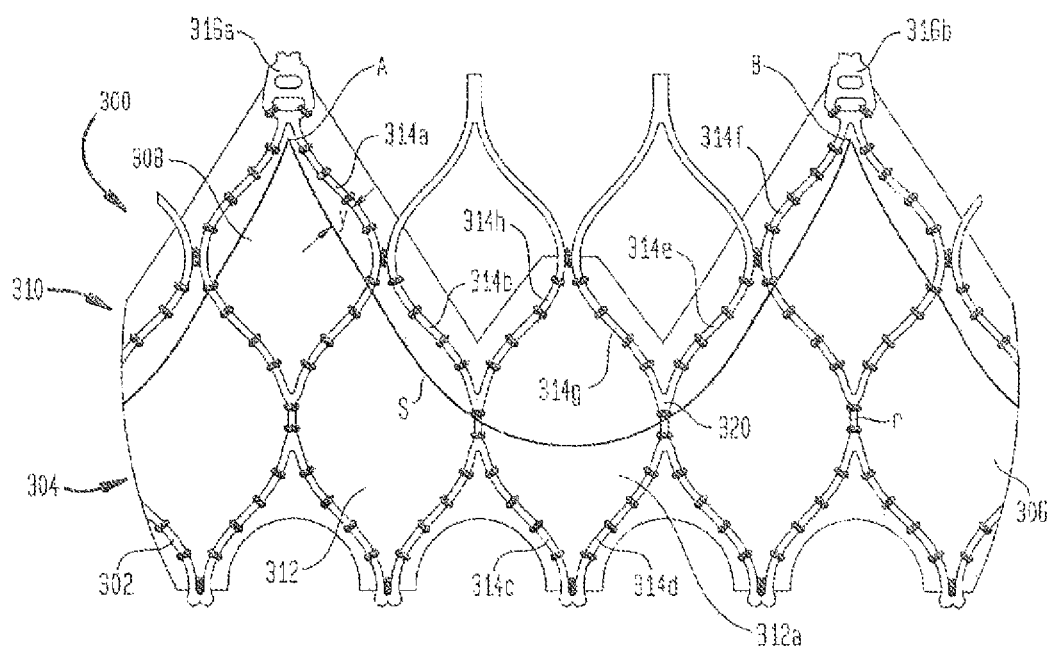
FIG. 3 is a partial developed view of the collapsible prosthetic heart valve of FIG. 2A showing the suturing pattern of the leaflets to the cuff.

FIGS. 2A, 2B and 3 illustrate one such embodiment in which the leaflets 308 have been attached by suturing substantially entirely to the cuff 306. In the illustrated embodiment, the leaflets 308 are coupled to the cuff 306 after they have been attached to the commissure features 316. It will be understood, however, that the order of attachment may be changed or varied as necessary by those skilled in the art.

FIGS. 2A and 2B illustrate a cuff 306 and one or more leaflets 308. Each leaflet 308 includes a proximal end 352 for attachment to the cuff 306 and a free distal end 354 for coapting with the other leaflets to form a closed valve. As seen in FIG. 2A, each leaflet 308 may be folded upon itself at the proximal end 352 to form a belly flap 356 for attaching the leaflet to the cuff 306. The belly flap 356 may be formed by folding the proximal edge of the leaflet 308 once over itself toward the cuff 306 so that the belly flap is disposed between a portion of the leaflet and the cuff. The width x of the belly flap 356 between folded edge 356*a* and free edge 356*b* may vary from valve to valve, and also within a valve. For example, the belly flap 356 may have a width x between about 0.1 mm and about 2.0 mm Variants of the belly flap 356 are also contemplated herein. For example, the belly flap 356 may be formed by folding the leaflet 308 more than once (e.g., twice, thrice or more). Additionally, the belly flap 356 may be formed along only a portion of the proximal edge of the leaflet 308 if the entire proximal edge will not be sutured to the cuff 306. Still further, the belly flap 356 may be formed by folding the proximal edge of the leaflet 308 away from the cuff 306, rather than toward the cuff as described above.

After folding each leaflet 308 to form a belly flap 356, the leaflets 308 may be attached to the cuff 306 in accordance with the attachment pattern shown in FIG. 3. For the purpose of clarity, the leaflet-cuff attachment pattern will be described with reference to FIG. 3 without showing a belly flap. It will be understood, however, that a belly flap as described above and shown in FIGS. 2A and 2B may be disposed either on the inner or lumenal side of the leaflet 308 or between the leaflet and the cuff 306.

The prosthetic heart valve 300 of FIG. 3 includes a stent or frame 302 having an annulus section 310 and an aortic section (not shown). Each of the annulus section 310 and the aortic section of the stent 302 includes a plurality of cells 312 connected to one another around the circumference of the stent. The annulus section 310 and the aortic section of the stent 302 may include one or more annular rows of cells 312 connected to one another. For instance, the annulus section 310 may have two annular rows of cells 312. When the prosthetic heart valve 300 is in the expanded condition, each cell 312 may be substantially diamond shaped. Regardless of its shape, each cell 312 is formed by a plurality of struts 314. For example, a cell 312 may be formed by four struts 314.

The stent 302 may include commissure features 316 connecting at least two cells 312 in the longitudinal direction of the stent. The commissure features 316 may include eyelets for facilitating the suturing of a valve assembly 304 to the stent 302.

A cuff 306 may be disposed on the lumenal surface of annulus section 310, on the ablumenal surface of the annulus section, or on both surfaces, and the cuff may cover all or part of either or both of the lumenal and ablumenal surfaces of the annulus section. FIG. 3 shows cuff 306 disposed on the lumenal surface of annulus section 310 so as to cover part of the annulus section while leaving another part thereof uncovered. In particular, the cuff 306 covers substantially all of the annulus section 310 between the proximal edge of stent 302 and the commissure features 316, but a much lesser area of the annulus section between the commissure features. The valve assembly 304 may further include a plurality of leaflets 308 which collectively function as a one-way valve.

As shown in FIG. 3, struts 314a, 314b, and 314c may be connected to one another in substantially end-to-end fashion diagonally along three cells 312, beginning with an end of the strut 314a connected to a commissure feature 316a and ending with an end of strut 314c connected to an end of strut 314d. Struts 314c and 314d are part of the same cell 312a. Struts 314d, 314e, and 314f may be connected to one another in substantially end-to-end fashion diagonally along three cells 312, beginning with an end of the strut 314f connected to a commissure feature 316b and ending with the connection between an end of strut 314d and an end of strut 314c. For the sake of completeness, cell 312a includes strut 314c connected to strut 314d at the bottom of the cell and struts 314g and 314h connected to one another at the top of the cell, as well as to struts 314d and 314c, respectively.

In addition to being connected to one another around the circumference of stent 302, cells 312 may be connected to one another in the longitudinal direction of the stent. Two adjacent struts, for example struts 314e and 314g, merge near the bottom of the cell before splitting off into two different struts. The meeting point where two struts 314 merge or where one strut 314 splits into two components is defined as an ancon 320. The ancons 320 in two longitudinally adjacent rows of cells 312 may be joined by runners r.

The plurality of leaflets 308 may be attached directly to the cuff 306 near struts 314a, 314b, 314e, and 314f, such as by suturing. As shown in FIG. 3, the leaflets 308 may be attached to cuff 306 just proximal of the aforementioned struts 314 along an attachment line S. Specifically, a distance y may be maintained between the attachment line S and the struts 314. This distance may be less than or equal to 2.0 mm, and may vary as necessary. By attaching the leaflets 308 to the cuff 306 in a pattern that follows the curvature of some of the struts 314, stress on the cuff 306 may be reduced while maintaining a degree of flexibility.

As described above, the attachment line S includes an initial descent from just proximal of commissure feature 316a and continues proximal of struts 314a and 314b while substantially maintaining a distance y from the struts. At the proximal end of strut 314b, the attachment line S begins to flatten out, passing through cell 312a, and then ascends proximal of struts 314e and 314f, maintaining substantially the same or a similar distance y from the struts, until it reaches a point just proximal of commissure feature 316b. Between the descending seam and the ascending seam, the attachment line crosses a pair of runners r1 and r2 and forms a vertex therebetween.

Figure 4:
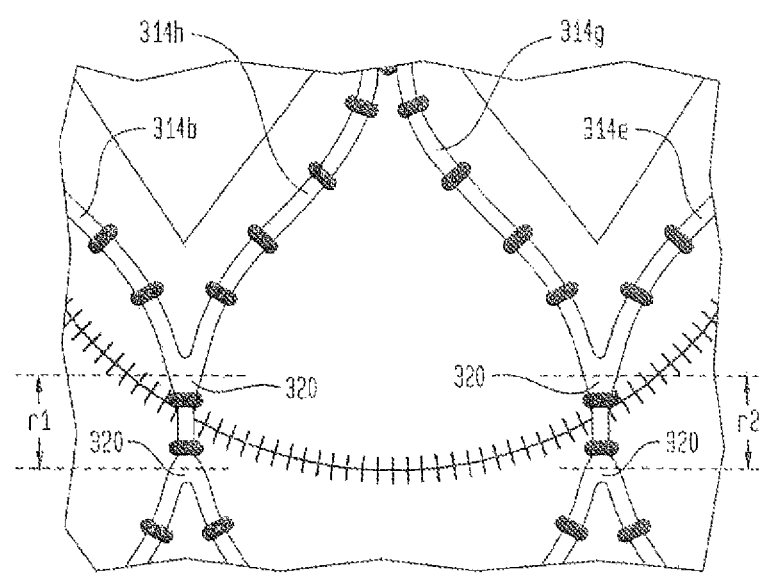
FIG. 4 is an enlarged side view of a portion of the collapsible prosthetic heart valve of FIG. 2A showing the runner region between ancons.

FIG. 4 shows runners r1 and r2 in more detail. As described above, the attachment line S generally descends from a point just proximal of commissure feature 316a, travels proximal of struts 314a and 314b, crosses runner r1, changes direction and crosses runner r2, and then ascends proximal of struts 314e and 314f until it reaches a point just proximal of commissure feature 316b.

The foregoing discussion describes the general pattern by which leaflets 308 may be attached directly to cuff 306. Having generally described the attachment pattern, the following description provides one exemplary method of suturing the leaflets 308 to the cuff 306. As will be understood by those of ordinary skill in the art, the description below is for one of many possible methods, and the distances, configurations and arrangements described are merely exemplary and not limiting. For example, instead of using a single suture around the perimeter of the valve assembly, leaflets 308 may be sutured to the cuff 306 using a plurality of sutures.

Initially, the leaflets 308 are aligned with the cuff 306 and struts 314 at the desired locations, typically in the annulus section 310. The ends of the distal free edge of each leaflet 308 are then sutured to both the cuff 306 and the stent 302 through the eyelets of an adjacent pair of commissure features 316. The belly of the leaflets 308 may then be sutured to the cuff 306 around the circumference of the heart valve 300 proximal of the commissure features 316.

With reference to FIG. 3, a first leaflet 308 may be sutured to the cuff 306 by first passing a suture from the ablumenal side of the cuff 306 to the lumenal side of the cuff approximately 0.5 mm to 2.0 mm proximal of a first commissure feature 316a. This location will be referred to as the origination stitch. A suture tail segment may be maintained at the origination stitch in order to tie to the end of the pattern after stitching around the circumference of the cuff 306 has been completed. The leaflet 308 may then be stitched to the cuff 306 using a series of whip stitches. Stitches from the ablumenal side to the lumenal side of the heart valve 300 pass through the cuff 306 only. Stitches from the lumenal side to the ablumenal side of the heart valve 300 pass through both layers of the leaflet 308 (e.g., the leaflet as well as the folded belly flap 356) and the cuff 306. Thus, with each whip stitch the suture is passed from the ablumenal side to the lumenal side of the heart valve 300 through the cuff 306 only and then through both layers of the leaflet 308 and the cuff 306 from the lumenal side of the valve to the ablumenal side thereof.

The stitch spacing and bite size may vary from about 0.5 mm to about 2.0 mm, and preferably is about 1.0 mm Stitches may be approximately perpendicular to the leaflet edge when viewed from the side of the valve 300. Beginning just proximal of commissure feature 316a, the sutures may travel approximately at a distance y proximal of struts 314a and 314b, across a first runner r1, form a vertex, across a second runner r2, and approximately at a distance y proximal of struts 314e and 314f until reaching a point just proximal of commissure feature 316b. The sutures may begin at a point A about 0.5 mm to about 2.0 mm proximal of commissure feature 316a, and may end at a point B, about 0.5 mm to about 2.0 mm proximal of commissure feature 316b.

Thus, between the first commissure feature 316a and the second commissure feature 316b, a substantially symmetrical parabola is formed by the suture line S. This parabolic pattern may be repeated between commissure features 316b and 316c and between commissure features 316c and 316a around the circumference of the cuff 306, ending at or near point A where the suture line S began. Upon returning to point A, the concluding tail of the suture line S may be tied to the origination stitch using a single double knot.

Figure 5:
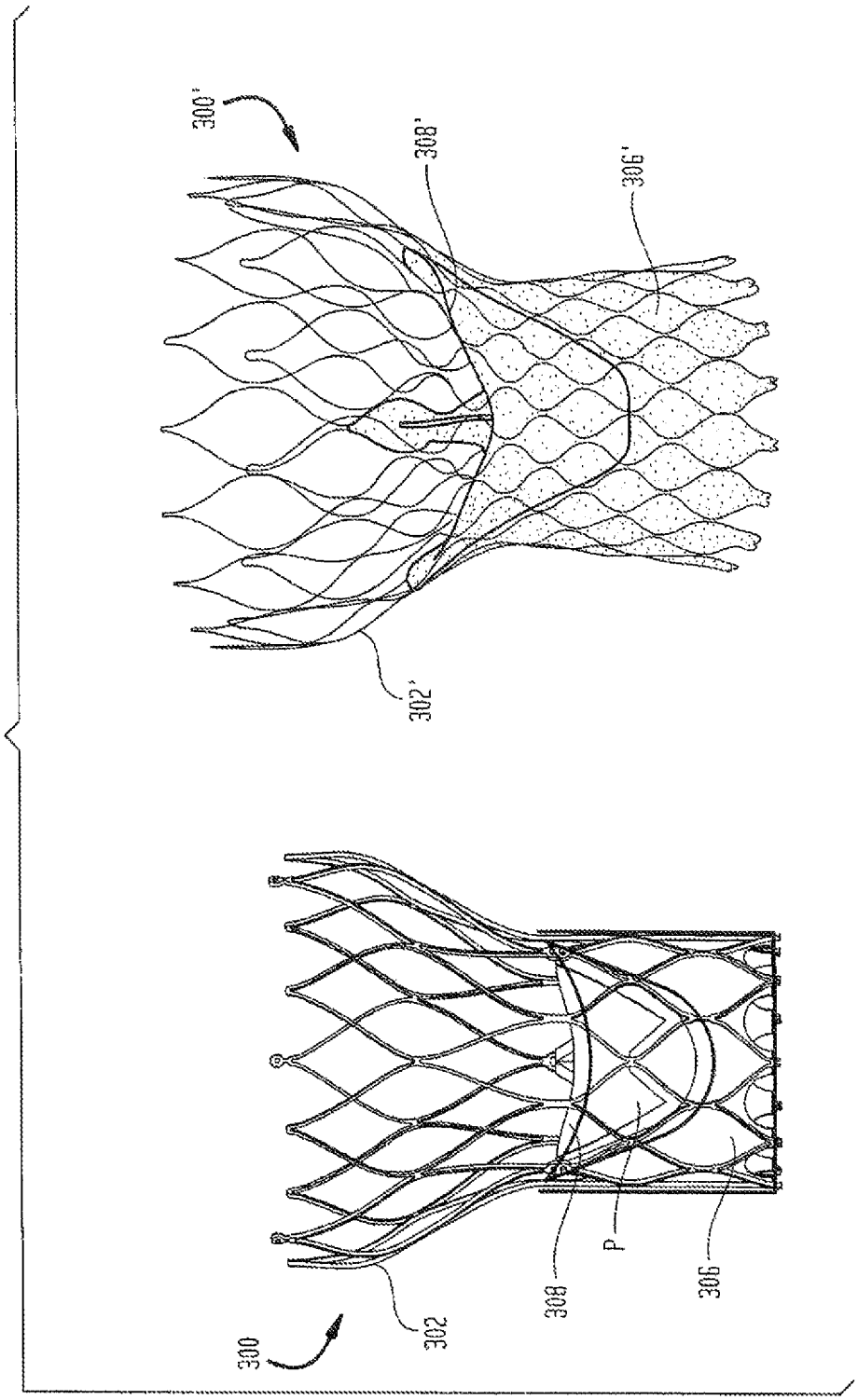
FIG. 5 depicts side views of a collapsible prosthetic heart valve according to an embodiment of the present invention having a pocket between the cuff and the leaflet, and a prior art device lacking such a pocket.

FIG. 5 shows a comparison between a heart valve 300 according to one embodiment of the present invention and a conventional heart valve 300'. As can be seen the heart valve 300 according to the present invention includes an enlarged cuff 306 that overlaps with a portion of the leaflets 308. In contrast, the heart valve 300' includes no such overlap between the leaflets 308' and the cuff 306'. Rather, the leaflets 308' and cuff 306' are attached to one another in an edge-to-edge fashion. The leaflet-cuff overlap provided by the heart valve 300 of the present invention forms a pocket P and allows for the suture pattern discussed above. Pocket P formed by the leaflet-cuff overlap minimizes perivalvular leakage and acts as a tissue buffer for improved durability. Compared to conventional devices, this configuration also provides a larger buffer against fretting corrosion. Thus, by providing an enlarged cuff, the stress on the cuff may be decreased, the durability of the cuff increased and the flexibility of the heart valve increased to allow for applications such as partial deployment of the heart valve, for example, for testing.

In this manner, by attaching the leaflets 308 to the cuff 306, a host of benefits as enumerated above, as well as others, may be achieved. Moreover, the description above provides one method by which stress on the cuff can be reduced. Namely, by suturing the leaflets to the cuff, maintaining the spacing between the suture line and the struts described above, and passing the sutures across the runners, the load on the cuff can be partially redistributed to the struts to prevent possible wear and/or failure. Thus, the foregoing embodiment describes one method for reducing stress on the cuff at critical junctions. This method provides a solution by suturing the leaflets to the cuff without providing a thicker cuff or using different materials for the cuff.

The above embodiment notwithstanding, it will be understood that the leaflets need not be coupled only (except for the commissure features) to the cuff. In other embodiments, instead of suturing the leaflets to only the cuff, selected regions of each leaflet, or the active proximal edge thereof, may be attached to the struts to relieve at least some of the stress on the cuff.

Figure 6:
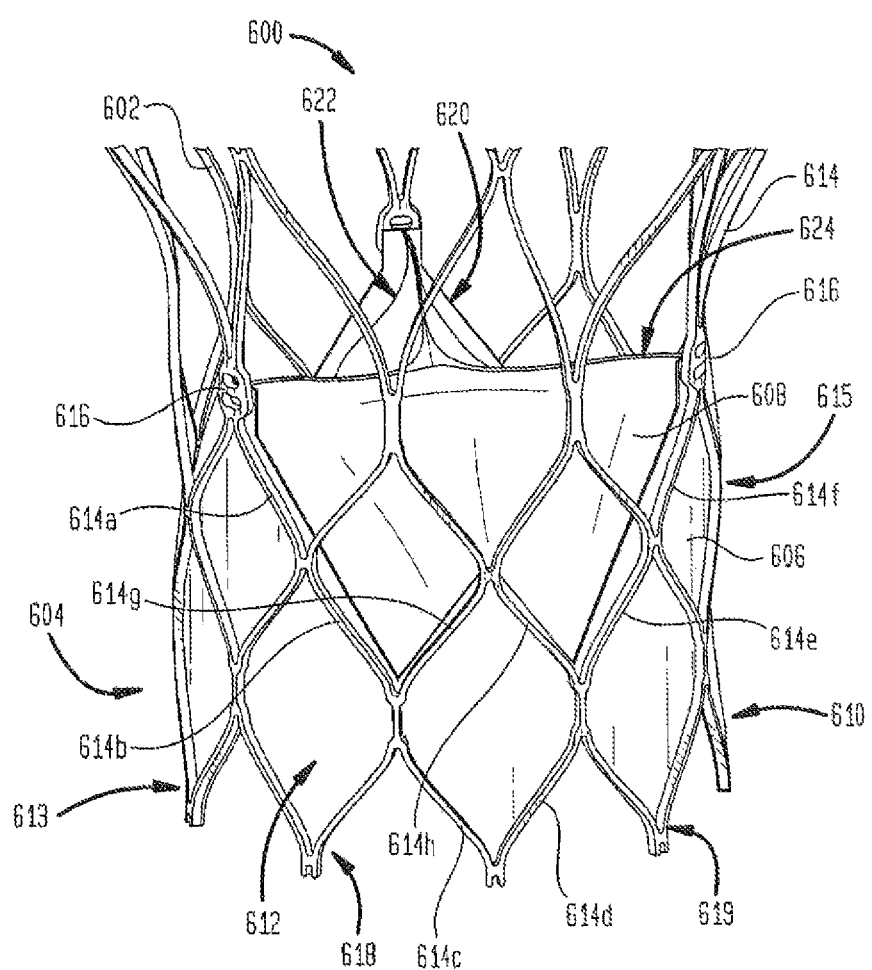
FIG. 6 is a partial side view of a collapsible prosthetic heart valve according to another embodiment of the present invention, showing the valve assembly attached to the stent.

FIG. 6 shows a collapsible prosthetic heart valve 600 according to another embodiment of the present invention. The prosthetic heart valve 600 is designed to replace the function of a native aortic valve of a patient. As discussed in detail below, the prosthetic heart valve has an expanded condition and a collapsed condition.

The prosthetic heart valve 600 includes a stent or frame 602, which may be wholly or partly formed of any of the materials noted above for forming stent 102. The stent 602 may have an annulus section 610 and an aortic section (not shown). Each of the annulus section 610 and the aortic section of the stent 602 includes a plurality of cells 612 connected to one another around the stent. The annulus section 610 and the aortic section of the stent 602 may include one or more annular rows of cells 612 connected to one another. For instance, the annulus section 610 may have two annular rows of cells 612. When the prosthetic heart valve 600 is in the expanded condition, each cell 612 may be substantially diamond shaped. Regardless of its shape, each cell 612 is formed by a plurality of struts 614. For example, a cell 612 may be formed by four struts 614.

The stent 602 may include commissure features 616 connecting at least two cells 612 in the longitudinal direction of the stent 602. The commissure features 616 may include eyelets to facilitate the suturing of a valve assembly 604 to the stent 602.

The prosthetic heart valve 600 also includes a valve assembly 604 attached inside the annulus section 610 of the stent 602. The valve assembly 604 may be formed from the same materials used to form valve assembly 104 described above. The valve assembly may include a cuff 606 disposed on the lumenal surface of annulus section 610, on the ablumenal surface of the annulus section, or on both surfaces. The cuff 606 may cover all or part of either or both of the lumenal and ablumenal surfaces of the annulus section. FIG. 6 shows cuff 606 disposed on the lumenal surface of the annulus section 610 so as to cover part of the annulus section while leaving another part thereof uncovered. In addition to the materials noted above for forming valve assembly 604, the cuff 606 may include ultra-high-molecular-weight polyethylene, as may any of the sutures described herein.

The valve assembly 604 may further include a plurality of leaflets 608 which collectively function as a one-way valve. A first edge 622 of each leaflet 608 may be attached to the stent 602 by any suitable attachment means, such as suturing, stapling, adhesives or the like. For example, the first edge 622 of each leaflet 608 may be sutured to the stent 602 by passing strings or sutures through the cuff 606 of the valve assembly 604. Optionally, portions of the first edge 622 of one or more leaflets 608 may be attached solely to the cuff 606. A second edge 624 of each leaflet 608 is free to coapt with the corresponding free edges of the other leaflets and thereby enables the leaflets to function collectively as a one-way valve.

Irrespective of the attachment means employed, the leaflets 608 may be attached to the stent 602 along at least some struts 614 of the stent to enhance the structural integrity of the valve assembly 604. As a consequence of this attachment, the struts 614 help support the leaflets 608 of the valve assembly 604 and may therefore reduce the strain in the leaflet-cuff junction.

As shown in FIG. 6, at least one leaflet 608 may be attached to the stent 602 so that its first edge 622 is disposed substantially along specific struts 614a, 614b, 614c, 614d, 614e and 614f located in the annulus section 610 of the stent. That is, the edge 622 is positioned in substantial alignment with struts 614a, 614b, 614c, 614d, 614e and 614f. Struts 614a, 614b, and 614c may be connected to one another in substantially end-to-end fashion diagonally along three cells 612, beginning with an end of the strut 614a connected to a commissure feature 616 and ending with an end of strut 614c connected to an end of strut 614d. Struts 614c and 614d are part of the same cell 612 and may collectively define approximately a right angle between them. Struts 614d, 614e, and 614f may be connected to one another in substantially end-to-end fashion diagonally along three cells 612, beginning with an end of the strut 614f connected to a commissure feature 616 and ending with the connection between an end of strut 614d and an end of strut 614c.

As discussed above, the leaflets 608 may be attached directly to and supported by the struts 614a, 614b, 614c, 614d, 614e and 614f, such as by suturing. In such event, the cuff 606 may perform little or no supportive function for the leaflets 608, and a cuff of minimum thickness may therefore be used. Minimizing the thickness of the cuff 606 results in a lower volume of the valve assembly 604 in the collapsed condition. This lower volume is desirable as it enables the prosthetic heart valve 600 to be implanted in a patient using a delivery device that is smaller than conventional delivery devices.

With continued reference to FIG. 6, the first or proximal end 618 of the cuff 606 may substantially follow the contour of the first or proximal end 619 of the stent 602, whereas the second or distal end 620 of the cuff 606 may be disposed substantially along at least some struts 614. More particularly, the second end 620 of the cuff 606 may be disposed substantially along struts 614a, 614b, 614e, 614f, 614g and 614h, as shown in FIG. 6, so as to form a zig-zag pattern of first or upper peaks and second or lower peaks. Strut 614g may be connected at one end to strut 614h, and at the other end to the intersection of struts 614b and 614c. Strut 614h may be connected at one end to strut 614g, and at the other end to the intersection of struts 614d and 614e. Struts 614c, 614d, 614g and 614h collectively form a single cell 612. Having the ends of the cuff 606 disposed substantially along the generally sinusoidal or zig-zag pattern of the stent struts 614 enables the stent struts to perform most of the supportive function for the leaflets 608, such that the cuff 606 performs little or no supportive function for the leaflets. Hence, the cuff 606 is not subjected to high stresses and is therefore less likely to fail during operation. In addition, since the material forming the stent struts 614 is stronger than the material forming the cuff 606, the stent struts 614 may perform the supportive function for the leaflets 608 better than the cuff 606.

As a result of the foregoing configuration, all of the cells 612 in the bottom annular row 613 of cells 612 may be entirely covered by the cuff 606. The cuff 606 may also entirely cover those cells 612 in a second annular row 615 that are located directly below the commissure feature 616. All of the other cells 612 in the stent 602 may be open or not covered by the cuff 606. Hence, there may be no cells 612 which are only partially covered by the cuff 606.

Figure 7:
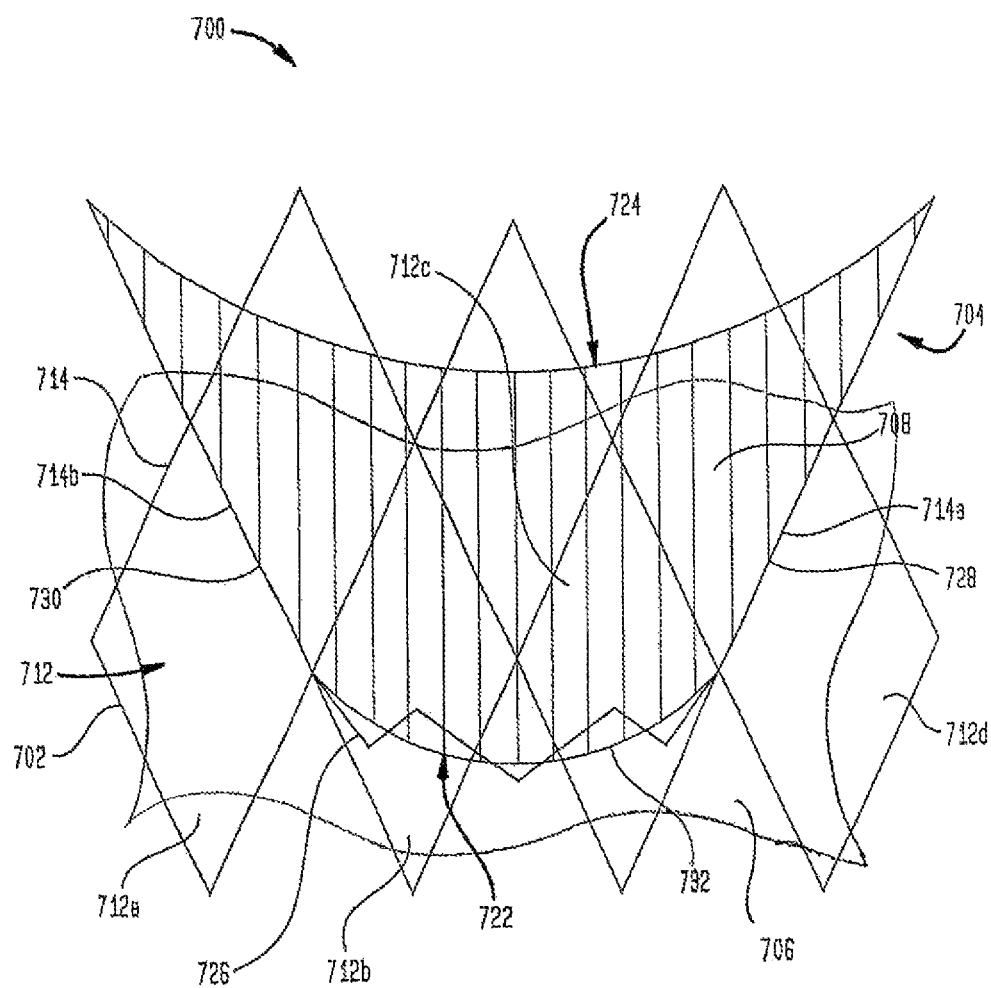
FIG. 7 is a highly schematic developed view of a portion of a collapsible prosthetic heart valve according to yet another embodiment of the present invention having leaflets of the valve assembly attached to the cuff in proximity to supplemental struts of the stent.

Referring to FIG. 7, a prosthetic heart valve 700 according to another embodiment of the present invention includes a stent or frame 702, which may be similar to stent 602. The stent 702 may include one or more annular rows of cells 712. Each cell 712 may be formed by a plurality of struts 714. For example, four struts 714 may form a single cell 712, which may be substantially diamond shaped when the stent 702 is in the expanded condition.

In addition to struts 714, the stent 702 may include one or more secondary or supplemental struts 726 extending across one or more cells 712. For example, one supplemental strut 726 may extend across two cells 712 located in the same annular row of cells. That is, supplemental strut 726 may extend from the point at which cell 712a joins cell 712b, across cells 712b and 712c, to the point at which cell 712c joins cell 712d. The supplemental struts 726 may have a serrated configuration, as shown in FIG. 7. Alternatively, the supplemental struts 726 may have a curved shape.

The prosthetic heart valve 700 further includes a valve assembly 704 attached inside the stent 702. The valve assembly 704 may be similar to valve assembly 604 and may include a cuff (not shown) and a plurality of leaflets 708 which collectively function as a one-way valve. A first edge 722 of each leaflet 708 may be attached to the stent 702 by any suitable attachment means, such as suturing, stapling, adhesives or the like. The leaflet 708 may be attached to the stent 702 through the cuff. Optionally, selected portions of the first edge 722 of one or more leaflets 708 may be attached solely to the cuff.

At least one leaflet 708 may be attached to the stent 702 so that the upper portions 728 and 730 of its edge 722 are disposed substantially along struts 714a and 714b, respectively. Such arrangement enables the stent struts 714 to perform most of the supportive function for the leaflet 708. As a result, the cuff performs little or no supportive function for the leaflet 708. Hence, the cuff is not subjected to high stresses and is therefore less likely to fail during operation. In addition, since the material forming the stent struts 714 is stronger than the material forming the cuff, the stent struts 714 may perform the supportive function for the leaflet 708 better than the cuff.

The serrated or curved configuration of supplemental struts 726 may be such as to approximate the curved shape of the lower portion 732 of the edge 722 of the leaflets 708. For example, if the supplemental strut 726 has a serrated configuration, the lower portion 732 of the edge 722 of each leaflet 708 may extend beyond some portions of the supplemental strut 726, while not quite reaching other portions of the supplemental strut. The greater the number of serrations supplemental strut 726 is formed with, the more closely the supplemental strut can approximate the shape of the lower portion 732 of the edge 722. In its lower portion 732, the edge 722 of each leaflet 708 may be attached to the cuff. The proximity of the lower portion 732 of the edge 722 to the supplemental struts 726 enables the supplemental struts to perform most of the supportive function for the lower portion of the edge 722 of the leaflets 708. A second edge 724 of each leaflet 708 is free to coapt with the corresponding free edges of the other leaflets and thereby enables the leaflets to function collectively as a one-way valve.

Figure 8B:
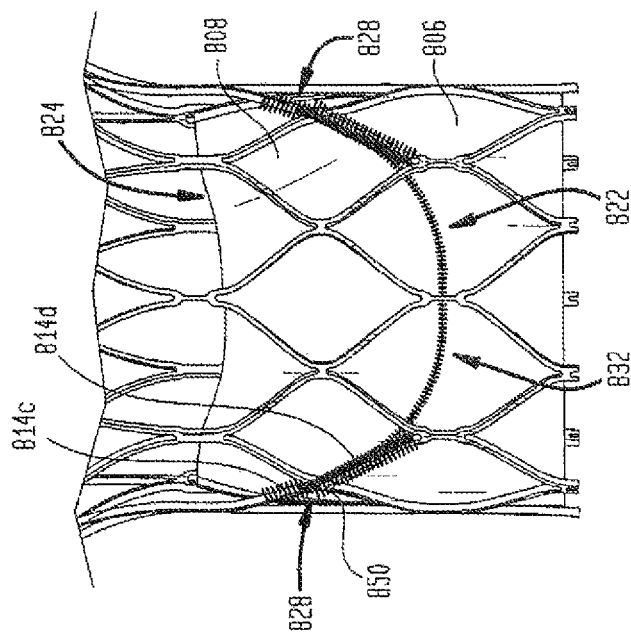
FIG. 8B is a partial side view of the collapsible prosthetic heart valve of FIG. 8A.
Figure 8A:
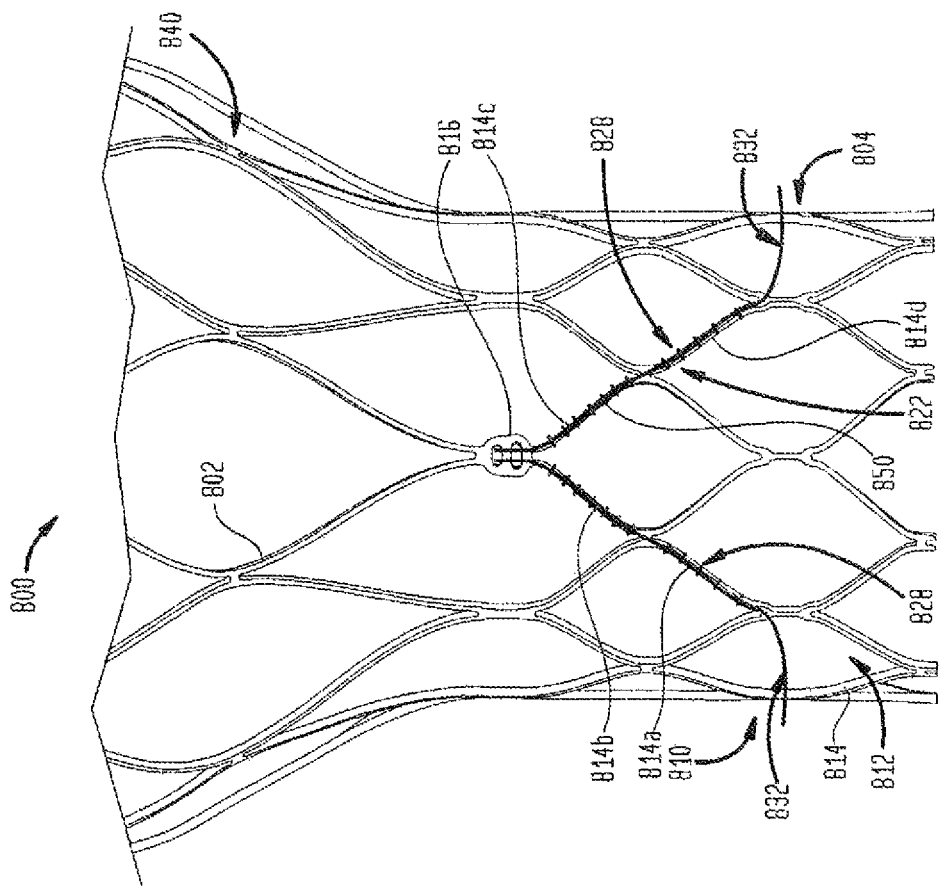
FIG. 8A is a developed view of a portion of a collapsible prosthetic heart valve according to a further embodiment of the present invention having the leaflets of the valve assembly attached to the stent and an edge of the leaflets disposed substantially along several stent struts.

With reference to FIGS. 8A and 8B, a prosthetic heart valve 800 according to yet another embodiment of the present invention includes a stent or frame 802, which may be similar to stent 602. The stent 802 may include an aortic section 840 and an annulus section 810. Each of the aortic section 840 and the annulus section 810 may include a plurality of cells 812 connected to one another in one or more annular rows. The cells 812 of the aortic section 840 may be larger than the cells of the annulus section 810. Each cell 812 is formed by a plurality of struts 814. For example, each cell 812 may be formed by four struts 814 and may be substantially diamond-shaped when the stent 802 is in an expanded condition. The stent 802 may further include one or more commissure features 816 for facilitating suturing of a valve assembly 804 to the stent. Each commissure feature 816 may interconnect two cells 812 in the same annular row and two cells in different annular rows.

The valve assembly 804 may be attached inside the stent 802. The valve assembly 804 may include a cuff 806 and a plurality of leaflets 808 which collectively function as a one-way valve. Each leaflet 808 includes an edge 822, portions of which are attached to the cuff 806 and other portions of which are attached to the stent 802, and a second free edge 824. An upper portion 828 of the edge 822 may be attached to the stent 802 so as to be disposed substantially along the path of certain struts 814 that lead to the commissure features 816. For example, an upper portion 828 of the edge 822 of at least one leaflet 808 may be attached to, and disposed substantially along, struts 814a and 814b. An upper portion 828 of the edge 822 of an adjacent leaflet 808 may be attached to, and disposed substantially along, struts 814c and 814d. As such, struts 814a, 814b, 814c and 814d help support these leaflets 808, thereby reducing the stress in the cuff 806. The upper portions 828 of the edges 822 of the leaflets 808 may be attached to the commissure feature 816 and struts 814a, 814b, 814c and 814d using sutures 850. Struts 814b and 814c may each have one end attached to a commissure feature 816 and each may be part of the same cell 812. Alternatively, struts 814b and 814c may be attached directly to one another. Struts 814a and 814b may be connected in an end-to-end fashion, and may be part of different cells 812 that are adjacent to one another. Similarly, struts 814c and 814d may be connected in an end-to-end fashion, and may be part of different cells 812 that are adjacent to one another. The lower portion 832 of the edge 822 of each leaflet 808 may be connected to the cuff 806.

With reference to FIGS. 9A and 9B, a collapsible prosthetic heart valve 900 according to an embodiment of the present invention includes a stent 902, which may be similar to stent 602. The stent 902 has collapsed and expanded conditions and includes a plurality of cells 912 connected to one another in annular rows around the stent. Each cell 912 is formed by a plurality of struts 914 and may be substantially diamond shaped when the stent 902 is in the expanded condition. For example, one cell 912 may be formed by four interconnected struts 914.

The stent 902 may further include one or more commissure features 916 that interconnect two adjacent cells 912 located in one annular row and two other cells 912 located in the next adjacent rows above and below the one row. The commissure features 916 may facilitate the suturing of a valve assembly 904 to the stent 902.

The valve assembly 904 may include a cuff 906 attached to the stent 902. As with all embodiments described herein, the cuff 906 may be disposed on the lumenal surface of the stent, the ablumenal surface of the stent, or on both surfaces. In addition to the cuff 906, the valve assembly 904 includes a plurality of leaflets 908 attached to the stent 902 and the cuff 906, and collectively defining a one-way valve. Each leaflet 908 includes a first edge 922 attached to both the cuff 906 and the stent 902 and a second free edge 924. At least one leaflet 908 may be attached to the cuff 906 and the stent 902 so that the upper portions 928 of its edge 922 are substantially disposed along the path of certain struts 914. As shown in FIGS. 9A and 9B, one upper portion 928 of the edge 922 of one leaflet 908 may be connected to a commissure feature 916 and may include an intermediate portion disposed along and connected to a strut 914b spaced from the commissure feature. Between strut 914b and commissure feature 916, the upper portion 928 of the edge 922 may be connected to the cuff 906 within the area of cell 912a. More particularly, an end section A of the upper portion 928 of the edge 922 may follow a substantially direct path between the commissure feature 916 and an end of stent strut 914b. Similarly, one upper portion 928 of the edge 922 of an adjacent leaflet 908 may be connected to the commissure feature 916 and may be disposed along and connected to a strut 914d spaced from the commissure feature. Between strut 914d and commissure feature 916, the upper portion 928 of the edge 922 of this leaflet may be connected to the cuff 906 within the area of cell 912a. That is, an end section A of the upper portion 928 of the edge 922 of this second leaflet may follow a substantially direct path between the commissure feature 916 and an end of stent strut 914d. The edges 922 of the leaflets may be connected to the commissure features 916 and to the struts 914b and 914d using sutures 950. The end sections A of the edges 922 of the leaflets 908 may be connected to the cuff 906 using sutures, bonding or other known techniques. The lower or middle portion 932 of the edge 922 of each leaflet 908 may be connected to the cuff 906 in a location not aligned with any strut.

With reference to FIGS. 10A and 10B, a prosthetic heart valve 1000 according to an embodiment of the present invention includes a stent or frame 1002 having an expanded condition and a collapsed condition. The stent 1002 may be similar to the stent 602 and includes a plurality of cells 1012 arranged in one or more annular rows. Each cell 1012 is formed by a plurality of struts 1014 and may be substantially diamond-shaped when the stent 1002 is in the expanded condition. For example, each cell 1012 may be formed by four interconnected struts 1014.

A valve assembly 1004 is attached inside the stent 1002 and may include a cuff 1006 and a plurality of leaflets 1008, which function as a one-way valve. The leaflets 1008 may be attached to the cuff 1006 and the stent 1002. Specifically, each leaflet 1008 may include an edge 1022 attached to the cuff 1006 and the stent 1002 and a free edge 1024. The upper portion 1028 of the edge 1022 may be attached to a commissure feature 1016 and to the cuff 1006 along a path substantially parallel to, but spaced from, some struts 1014. More particularly, one section of the upper portion 1028 of the edge 1022 of one leaflet 1008 may be disposed substantially along a direct path between commissure feature 1016 and a runner 1015a between two adjacent cells 1012 in annular bottom row 1017 of cells. One section of the upper portion 1028 of the edge 1022 of an adjacent leaflet 1008 may be disposed substantially along a direct path between commissure feature 1016 and a runner 1015b between two adjacent cells 1012 in the bottom row 1017 of cells. The upper portions 1028 of the edges 1022 may be spaced from some struts 1014 by a substantially uniform distance, i.e., the upper portions of the edges may be substantially parallel to these struts. For example, at least part of the upper portion 1028 of the edge 1022 of one leaflet 1008 may be spaced a substantially uniform distance from struts 1014a and 1014b, while the upper portion 1028 of the edge 1022 of the adjacent leaflet may be spaced a substantially uniform distance from struts 1014c and 1014d. This distance may be about 2 mm in preferred embodiments. The lower portions 1032 of the first edge 1022 of each leaflet 1008 may intersect the runners 1015 along the bottom row 1017 of cells 1012.

In operation, any of the embodiments of the prosthetic heart valve described above may be used to replace a native heart valve, such as the aortic valve. The prosthetic heart valve may be delivered to the desired site (e.g., near a native aortic annulus) using any suitable delivery device. During delivery, the prosthetic heart valve is disposed inside the delivery device in the collapsed condition. The delivery device may be introduced into a patient using a transfemoral, transapical or transseptal approach. Once the delivery device has reached the target site, the user may deploy any of the prosthetic heart valves described above. Upon deployment, the prosthetic heart valve expands into secure engagement within the native aortic annulus. When the prosthetic heart valve has been properly positioned inside the heart, it works as a one-way valve, allowing blood to flow in one direction and preventing blood from flowing in the opposite direction.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
a stent having a collapsed condition and an expanded condition, the stent including a plurality of cells arranged in annular rows around a circumference of the stent, each cell being formed by a plurality of struts, each cell in a first annular row of cells including a runner connecting one cell in the first annular row to an adjacent cell in the first annular row;
a plurality of commissure features disposed on the stent; and
a valve assembly secured to the stent and including a cuff and a plurality of leaflets, each leaflet including a first edge adjacent to the cuff and a free edge spaced apart from the cuff, the first edge of each leaflet having ends, a middle portion and intermediate portions between the middle portion and the ends, the ends being connected to a respective pair of the commissure features, a first one of the intermediate portions being connected only to the cuff along a descending path spaced from a first group of the struts, a second one of the intermediate portions being connected only to the cuff along an ascending path spaced from a second group of the struts, and the middle portion crossing one of the runners and being connected only to the cuff between the descending path and the ascending path.

2. The prosthetic heart valve as claimed in claim 1, wherein each of the cells has substantially a diamond shape in the expanded condition.

3. The prosthetic heart valve as claimed in claim 1, wherein the descending path extends substantially parallel to the first group of struts.

4. The prosthetic heart valve as claimed in claim 3, wherein the descending path is spaced about 2 mm or less from the first group of struts.

5. The prosthetic heart valve as claimed in claim 3, wherein the ascending path extends substantially parallel to the second group of struts.

6. The prosthetic heart valve as claimed in claim 5, wherein the ascending path is spaced about 2 mm or less from the second group of struts.

7. The prosthetic heart valve as claimed in claim 1, wherein the middle portion of the first edge of each leaflet crosses two of the runners.

8. The prosthetic heart valve as claimed in claim 7, wherein the two runners are in the first annular row of cells.

9. The prosthetic heart valve as claimed in claim 1, wherein each of the leaflets is folded along a fold line at a predetermined distance from the first edge to define a belly flap folded against a remaining portion of the leaflet.

10. A prosthetic heart valve, comprising:
a stent having a collapsed condition and an expanded condition, the stent including a plurality of cells arranged in annular rows around a circumference of the stent, each cell being formed by a plurality of struts, each cell in a first annular row of cells including a runner connecting one cell in the first annular row to an adjacent cell in the first annular row;
a plurality of commissure features disposed on the stent, each of the commissure features being connected to a respective one of the cells positioned directly below the commissure feature; and
a valve assembly secured to the stent and including a cuff and a plurality of leaflets, each of the leaflets including a first edge adjacent to the cuff and a free edge spaced apart from the cuff, the first edge having ends, a middle portion and intermediate portions between the middle portion and the ends, one end of a first one of the leaflets being connected to a first one of the commissure features, one intermediate portion of the first leaflet being connected only to the cuff along a first descending path within the cell directly below the first commissure feature, the first descending path being spaced from a first one of the struts forming the cell directly below the first commissure feature, one end of a second one of the leaflets adjacent the first leaflet being connected to the first commissure feature, and one intermediate portion of the second leaflet being connected only to the cuff along a second descending path within the cell directly below the first commissure feature, the second descending path being spaced from a second one of the struts forming the cell directly below the first commissure feature.

11. The prosthetic heart valve as claimed in claim 10, wherein each of the cells has substantially a diamond shape in the expanded condition.

12. The prosthetic heart valve as claimed in claim 10, wherein the first descending path extends substantially parallel to the first one of the struts.

13. The prosthetic heart valve as claimed in claim 12, wherein the first descending path is spaced about 2 mm or less from the first one of the struts.

14. The prosthetic heart valve as claimed in claim 12, wherein the second descending path extends substantially parallel to the second one of the struts.

15. The prosthetic heart valve as claimed in claim 14, wherein the second descending path is spaced about 2 mm or less from the second one of the struts.

16. The prosthetic heart valve as claimed in claim 10, wherein the cuff has a proximal end and a distal end, the distal end defining a plurality of first peaks and a plurality of second peaks, the first peaks and the second peaks intersecting at intersection points, each of the first peaks extending between a pair of the intersection points and a respective one of the commissure features, and the second peaks extending between adjacent ones of the first peaks.

17. The prosthetic heart valve as claimed in claim 16, wherein each of the first peaks extends from the pair of intersection points by a first distance to the respective commissure feature, and each of the second peaks extends from a pair of the intersection points by a distance less than the first distance.

18. The prosthetic heart valve as claimed in claim 10, wherein each of the leaflets is folded along a fold line at a predetermined distance from the first edge to define a belly flap folded against a remaining portion of the leaflet.

* * * * *